US010975126B1

(12) United States Patent
Elsayed et al.

(10) Patent No.: US 10,975,126 B1
(45) Date of Patent: Apr. 13, 2021

(54) MERS-COV INHIBITOR PEPTIDES

(71) Applicant: KING FAISAL UNIVERSITY, Al-Ahsa (SA)

(72) Inventors: Mahmoud Kandeel Elsayed, Al-Ahsa (SA); Abdulla Yousef Al-Taher, Al-Ahsa (SA); Hyung-Joo Kwon, Al-Ahsa (SA); Mohammed Al-Nazawi, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 16/857,136

(22) Filed: Apr. 23, 2020

(51) Int. Cl.
*C07K 14/005* (2006.01)
*A61K 38/00* (2006.01)

(52) U.S. Cl.
CPC ............ *C07K 14/005* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,623,741 | B1 | 9/2003 | Antczak et al. |
| 8,828,407 | B2 | 9/2014 | Britton et al. |
| 2018/0037636 | A1 | 2/2018 | Walensky et al. |
| 2019/0256579 | A1 | 8/2019 | Graham |

FOREIGN PATENT DOCUMENTS

| | | |
|---|---|---|
| CN | 104072592 A | 10/2014 |
| CN | 107022008 A | 8/2017 |
| CN | 108395471 A | 8/2018 |
| CN | 110128510 A | 8/2019 |

OTHER PUBLICATIONS

Lu et al. ('Structure-based discovery of Middle East respiratory syndrome coronavirus fusion inhibitor' Nature Communications Jan. 28, 2014 pp. 1-12) (Year: 2014).*

Kandeel, M. et al., "Molecular Dynamics of Middle East Respiratory Syndrome Coronavirus (MERS CoV) Fusion Heptad Repeat Trimers," Computational Biology and Chemistry, 75: pp. 205-212, (2018).

Hilchie, A. L. et al., "Immune Modulation by Multifaceted Cationic Host Defense (Antimicrobial) Peptides," Nature Chemical Biology, (9): pp. 761-768, (2013).

Lu, L. et al., "Structure-based Discovery of Middle East Respiratory Syndrome Coronavirus Fusion Inhibitor," Nature Communications, 5:3067 (2014).

Mustafa, S. et al., "Current Treatment Options and the Role of Peptides as Potential Therapeutic Components for Middle East Respiratory Syndrome (MERS): A Review," Journal of Infection and Public Health, (11): pp. 9-17, (2017).

Dehouck, Y. et al., "BeAtMuSiC: Prediction of changes in protein-protein binding affinity on mutations," Nucleic Acids Research, 41: pp. W333-W339 (2013).

Yamamoto M. et al., "Identification of Nafamostat as a Potent Inhibitor of Middle East Respiratory Syndrome Coronavirus S Protein-Mediated Membrane Fusion Using the Split-Protein-Based Cell-Cell Fusion Assay," Antimicrob. Agents Chemother. 60(11): pp. 6532-6539 (2016).

Park, B. K. et al., "Generation and characterization of a monoclonal antibody against MERS-CoV targeting the spike-protein using a synthetic peptide epitope-CpG-DNA-liposome complex," BMB Rep. 52(6): pp. 397-402 (2019).

* cited by examiner

*Primary Examiner* — Ronald T Niebauer
(74) *Attorney, Agent, or Firm* — Nath, Goldberg & Meyer; Richard C. Litman

(57) ABSTRACT

The MERS-CoV inhibitor peptides include a set of peptides designed by modification or mutation of a wild type MERS-CoV fusion protein. The MERS-CoV inhibitor peptides are capable of inhibition of MERS-CoV membrane fusion, and thereby may prevent or slow the spread of MERS-CoV infections. Thus, the MERS-CoV inhibitor peptides may be used in pharmaceuticals to prevent and/or treat MERS-CoV infection. The pharmaceuticals may be formulated to comprise at least one of the MERS-CoV inhibitor peptides and a carrier, or they may include one or more expression systems capable of promoting cellular expression of one or more MERS-CoV inhibitor peptides. The MERS-CoV inhibitor peptides may also be used as reagents for MERS-CoV inhibition assays as a standard or reference inhibitors.

5 Claims, 6 Drawing Sheets

Specification includes a Sequence Listing.

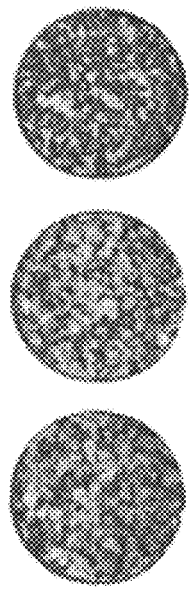
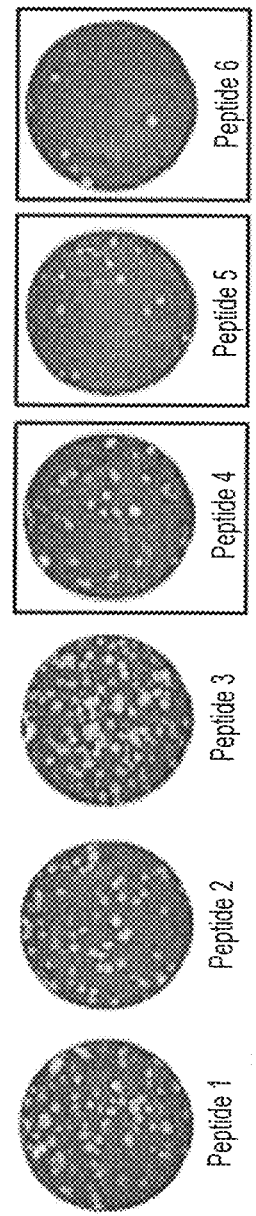
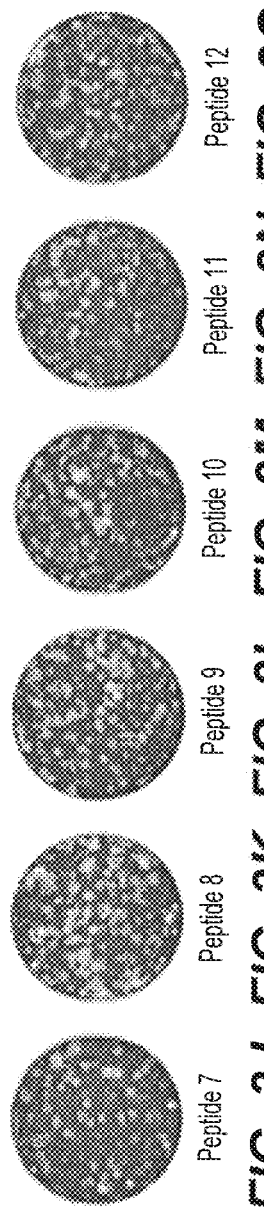

```
                       SEQUENCE LISTING

<160> NUMBER OF SEQ ID NOS: 13

<210> SEQ ID NO 1
<211> LENGTH: 36
<212> TYPE: PRT
<213> ORGANISM: Middle East Respiratory Syndrome Coronavirus

<400> SEQUENCE: 1

Ser Leu Thr Gln Ile Asn Thr Thr Leu Leu Asp Leu Thr Tyr Glu Met
1               5                   10                  15

Leu Ser Leu Gln Gln Val Val Lys Ala Leu Asn Glu Ser Tyr Ile Asp
            20                  25                  30

Leu Lys Glu Leu
        35

<210> SEQ ID NO 2
<211> LENGTH: 36
<212> TYPE: PRT
<213> ORGANISM: Middle East Respiratory Syndrome Coronavirus

<400> SEQUENCE: 2

Ser Leu Thr Gln Ile Asn Thr Thr Leu Leu Asp Leu Thr Tyr Glu Met
1               5                   10                  15

Leu Ser Leu Gln Gln Val Val Lys Ala Leu Asn Glu Ser Tyr Ile Asp
            20                  25                  30

Leu Lys His Leu
        35

<210> SEQ ID NO 3
<211> LENGTH: 36
<212> TYPE: PRT
<213> ORGANISM: Middle East Respiratory Syndrome Coronavirus

<400> SEQUENCE: 3

Ser Leu Thr Gln Ile Asn Thr Thr Leu Leu Asp Leu Thr Tyr Glu Met
1               5                   10                  15

Lys Ser Leu Gln Gln Val Val Lys Ala Leu Asn Glu Ser Tyr Ile Asp
            20                  25                  30

Leu Lys Glu Leu
        35

<210> SEQ ID NO 4
<211> LENGTH: 36
```

```
<212> TYPE: PRT
<213> ORGANISM: Middle East Respiratory Syndrome Coronavirus

<400> SEQUENCE: 4

Ser Leu Thr Gln Ile Asn Trp Thr Leu Leu Asp Leu Thr Tyr Glu Met
1               5                   10                  15

Glu Ser Leu Gln Gln Val Val Lys Ala Leu Asn Glu Ser Tyr Ile Asp
            20                  25                  30

Leu Lys Glu Leu
        35

<210> SEQ ID NO 5
<211> LENGTH: 35
<212> TYPE: PRT
<213> ORGANISM: Middle East Respiratory Syndrome Coronavirus

<400> SEQUENCE: 5

Ser Leu Thr Gln Ile Asn Trp Thr Leu Leu Asp Leu Thr Tyr Glu Met
1               5                   10                  15

Glu Ser Leu Gln Gln Val Val Lys Ala Leu Asn Glu Tyr Tyr Ile Asp
            20                  25                  30

Leu Lys Glu
        35

<210> SEQ ID NO 6
<211> LENGTH: 36
<212> TYPE: PRT
<213> ORGANISM: Middle East Respiratory Syndrome Coronavirus

<400> SEQUENCE: 6

Ser Leu Thr Gln Ile Asn Trp Thr Leu Leu Asp Leu Thr Tyr Glu Met
1               5                   10                  15

Glu Ser Leu Gln Gln Val Val Lys Ala Leu Asn Glu Tyr Tyr Ile Asp
            20                  25                  30

Leu Lys His Leu
        35

<210> SEQ ID NO 7
<211> LENGTH: 36
<212> TYPE: PRT
<213> ORGANISM: Middle East Respiratory Syndrome Coronavirus

<400> SEQUENCE: 7

Ser Leu Thr Gln Ile Asn Trp Thr Leu Leu Asp Leu Thr Tyr Glu Met
1               5                   10                  15

Glu Ser Leu Gln Gln Val Met Lys Ala Leu Asn Glu Tyr Tyr Ile Asp
            20                  25                  30

Leu Lys His Leu
        35

<210> SEQ ID NO 8
<211> LENGTH: 36
<212> TYPE: PRT
<213> ORGANISM: Middle East Respiratory Syndrome Coronavirus

<400> SEQUENCE: 8

Ser Leu Thr Gln Ile Asn Thr Thr Leu Leu Asp Leu Glu Tyr Glu Met
1               5                   10                  15

Leu Ser Leu Gln Gln Val Val Lys Ala Leu Asn Glu Ser Tyr Ile Asp
            20                  25                  30
```

Leu Lys Glu Leu
        35

<210> SEQ ID NO 9
<211> LENGTH: 36
<212> TYPE: PRT
<213> ORGANISM: Middle East Respiratory Syndrome Coronavirus

<400> SEQUENCE: 9

Ser Leu Thr Gln Ile Asn Thr Thr Leu Leu Asp Leu Glu Tyr Glu Met
1               5                   10                  15

Arg Ser Leu Gln Gln Val Val Lys Ala Leu Asn Glu Ser Tyr Ile Asp
            20                  25                  30

Leu Lys Glu Leu
        35

<210> SEQ ID NO 10
<211> LENGTH: 36
<212> TYPE: PRT
<213> ORGANISM: Middle East Respiratory Syndrome Coronavirus

<400> SEQUENCE: 10

Ser Leu Thr Gln Ile Asn Thr Thr Leu Leu Asp Leu Glu Tyr Glu Met
1               5                   10                  15

Arg Ser Leu Glu Glu Val Val Lys Ala Leu Asn Glu Ser Tyr Ile Asp
            20                  25                  30

Leu Lys Glu Leu
        35

<210> SEQ ID NO 11
<211> LENGTH: 36
<212> TYPE: PRT
<213> ORGANISM: Middle East Respiratory Syndrome Coronavirus

<400> SEQUENCE: 11

Ser Leu Thr Gln Ile Asn Thr Thr Leu Leu Asp Leu Glu Tyr Glu Met
1               5                   10                  15

Arg Ser Leu Glu Glu Val Val Lys Lys Leu Asn Glu Ser Tyr Ile Asp
            20                  25                  30

Leu Lys Glu Leu
        35

<210> SEQ ID NO 12
<211> LENGTH: 36
<212> TYPE: PRT
<213> ORGANISM: Middle East Respiratory Syndrome Coronavirus

<400> SEQUENCE: 12

Ser Leu Thr Gln Ile Asn Thr Thr Leu Leu Asp Leu Glu Tyr Glu Met
1               5                   10                  15

Arg Ser Leu Glu Glu Val Val Lys Lys Leu Asn Glu Ser Tyr Ile Asp
            20                  25                  30

Glu Lys Glu Leu
        35

<210> SEQ ID NO 13
<211> LENGTH: 36
<212> TYPE: PRT
<213> ORGANISM: Middle East Respiratory Syndrome Coronavirus
<220> FEATURE:
<221> NAME/KEY: misc_feature
<222> LOCATION: (17)..(17)

-continued

<223> OTHER INFORMATION: Xaa can be any naturally occurring amino acid

<400> SEQUENCE: 13

```
Ser Leu Thr Gln Ile Asn Thr Thr Leu Leu Asp Leu Thr Tyr Glu Met
1               5                   10                  15

Xaa Ser Leu Gln Gln Val Val Lys Ala Leu Asn Glu Ser Tyr Ile Asp
            20                  25                  30

Leu Lys Glu Leu
        35
```

US 10,975,126 B1

MERS-COV INHIBITOR PEPTIDES

INCORPORATION BY REFERENCE OF MATERIAL SUBMITTED IN COMPUTER READABLE FORM

The Applicants hereby incorporate by reference the sequence listing contained in the ASCII text filed titled 32087__14_Sequence_Listing_ST25.txt, created Mar. 13, 2020, and having 6 KB of data.

BACKGROUND

1. Field

The disclosure of the present patent application relates to anti-RNA virus peptides, and particularly to a MERS-CoV inhibitor peptides.

2. Description of the Related Art

Middle East Respiratory Syndrome Coronavirus (MERS-CoV), alternatively called HCoV-EMC/2012, causes severe respiratory illness with symptoms including fever, cough, and shortness of breath. Some subjects also experience diarrhea, nausea, or vomiting. MERS-CoV is fatal for 3-4 of every ten people infected. Currently, there is no vaccine approved to prevent transmission of MERS-CoV and there is no specific antiviral treatment suggested for MERS-CoV infection. Thus, preventative measures generally involve routine avoidance of behaviors likely to lead to infection (hand washing, covering the nose and mouth when sneezing, avoiding contact with the eyes, nose, or mouth, and avoiding direct contact with infected individuals). Care may include general medical support for basic vital organ function, but does not include any medications targeting MERS-CoV specifically.

MERS-CoV is an enveloped virus, which means a viral envelope protein must identify a host receptor and initial membrane fusion in order for the virus to enter and infect host cells (membrane fusion may be either at the plasma membrane or in endosomes after endocytosis). MERS-CoV accomplishes membrane fusion through interactions between the virus'S-protein and host marker CD26.

Recent work in this field has focused on developing monoclonal antibodies to MERS-CoV, or screening pre-existing small molecule libraries to look for compounds that inhibit S-protein mediated membrane fusion. In addition, a peptide sequence found in the HR2 region of wild type MERS-CoV has been shown to have some limited inhibitory effect on MERS-CoV membrane fusion. However, this prior work has yet to deliver a pharmaceutical capable of either preventing MERS-CoV infection or treating an infected subject.

Thus, MERS-CoV inhibitor peptides solving the aforementioned problems are desired.

SUMMARY

The MERS-CoV inhibitor peptides include a set of peptides designed by modification or mutation of a wild type MERS-CoV fusion protein. The MERS-CoV inhibitor peptides are capable of inhibition of MERS-CoV infection in cells and may be used to prevent and/or treat MERS-CoV infection. The MERS-CoV inhibitor peptides may also be used as reagents for MERS-CoV inhibition assays as a standard or reference inhibitors.

An embodiment of the present subject matter is directed to a pharmaceutical composition including one or more of the MERS-CoV inhibitor peptides and a pharmaceutically acceptable carrier.

An embodiment of the present subject matter is directed to a method of making a pharmaceutical composition including mixing one or more of the MERS-CoV inhibitor peptides under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to compositions including one or more of the MERS-CoV inhibitor peptides and one or more expression systems. The expression system may be a viral based expression system, a plasmid based expression system, or any other expression system suitable for causing or enhancing expression of the MERS-CoV inhibitor peptides in a bacterium, yeast, or mammalian cell. The expression system may include a promoter sequence and DNA or RNA encoding one or more of the MERS-CoV inhibitor peptides.

An embodiment of the present subject matter is directed to methods of inhibiting MERS-CoV infection, preventing MERS-CoV transmission, and/or treating a MERS-CoV infection, including administering to a subject in need thereof a therapeutically effective amount of a pharmaceutical composition according to the present subject matter. In a further embodiment, the methods of inhibiting MERS-CoV infection may include preventing MERS-CoV infection of a cell.

An embodiment of the present subject matter is directed to methods of using the MERS-CoV inhibitor peptides as reference agents to evaluate inhibition by other candidates against MERS CoV. These methods may include using the MERS-CoV inhibitor peptides as reference agents in Cell-Cell Fusion Assays, Viral Plaque Formation Assays, Viral RNA Quantitation Assays, or the like.

These and other features of the present subject matter will become readily apparent upon further review of the following specification.

BRIEF DESCRIPTION OF THE DRAWINGS

FIGS. 3A-3O depict the results of a Plaque Reduction Assay for MERS-CoV treated with 10 µM Peptides 1-12.

Similar reference characters denote corresponding features consistently throughout the attached drawings.

DETAILED DESCRIPTION OF THE PREFERRED EMBODIMENTS

Figure 1:
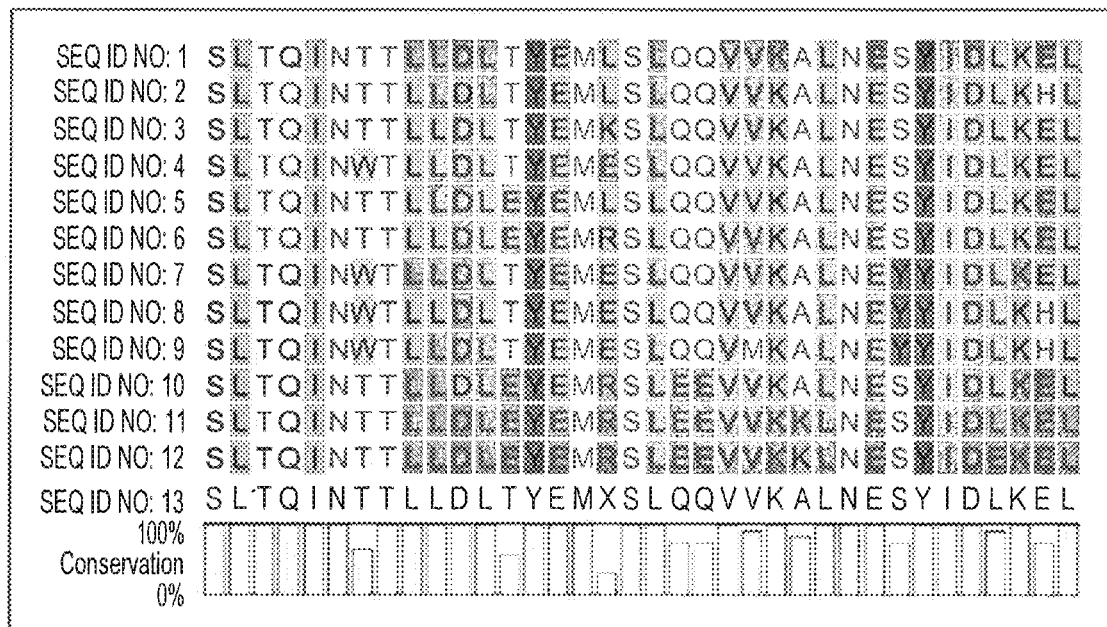
FIG. 1 depicts a sequence alignment of Peptides 1-12 (SEQ ID NOs:1-12 respectively) and of the consensus sequence (SEQ ID NO: 13) and displays the % conservation of each amino acid in the aligned sequences.

The MERS-CoV inhibitor peptides include a set of peptides designed by modification or mutation of a wild type MERS-CoV fusion protein. The MERS-CoV inhibitor peptides are capable of inhibition of MERS-CoV infection in cells and may be used to prevent and/or treat MERS-CoV infection. The MERS-CoV inhibitor peptides may also be used as reagents for MERS-CoV inhibition assays as a standard or reference inhibitors.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

An embodiment of the present subject matter is directed to a pharmaceutical composition comprising one or more of the MERS-CoV inhibitor peptides and a pharmaceutically acceptable carrier.

An embodiment of the present subject matter is directed to a method of making a pharmaceutical composition including mixing one or more of the MERS-CoV inhibitor peptides with a pharmaceutically acceptable carrier. For example, the method of making a pharmaceutical composition can include mixing a MERS-CoV inhibitor peptide under sterile conditions with a pharmaceutically acceptable carrier with preservatives, buffers, and/or propellants to create the pharmaceutical composition.

An embodiment of the present subject matter is directed to a pharmaceutical composition including one or more of the MERS-CoV inhibitor peptides. To prepare the pharmaceutical composition, one or more of the MERS-CoV inhibitor peptides, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. One or more of the MERS-CoV inhibitor peptides can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of a MERS-CoV inhibitor peptide or an amount effective to treat a disease, such as a coronavirus infection, may be determined initially from the Examples described herein and adjusted for specific targeted diseases using routine methods.

An embodiment of the present subject matter is directed to compositions including one or more of the MERS-CoV inhibitor peptides and one or more expression systems. The expression system may be a viral based expression system, a plasmid based expression system, or any other expression system suitable for causing or enhancing expression of the MERS-CoV inhibitor peptides in a bacterium, yeast, or mammalian cell. The expression system may include a promoter sequence and DNA or RNA encoding one or more of the MERS-CoV inhibitor peptides.

An embodiment of the present subject matter is directed to methods of using the MERS-CoV inhibitor peptides as reference agents to evaluate inhibition by other candidates against MERS CoV. These methods may include using the MERS-CoV inhibitor peptides as reference agents in Cell-Cell Fusion Assays, Viral Plaque Formation Assays, Viral RNA Quantitation Assays, or the like.

The MERS-CoV inhibitor peptides can be administered to a subject in need thereof. In an embodiment, the MERS-CoV inhibitor peptides can be administered to a subject in need thereof to inhibit MERS-CoV infection, preventing MERS-CoV transmission, and/or treating a MERS-CoV infection.

An embodiment of the present subject matter is directed to a method of inhibiting MERS-CoV infection, preventing MERS-CoV transmission, and/or treating a MERS-CoV infection, comprising administering to a subject in need thereof a therapeutically effective amount of the pharmaceutical composition according to the present subject matter.

The MERS-CoV inhibitor peptides or pharmaceutical compositions thereof can be administered to a subject by any suitable route. For example, the compositions can be administered nasally, rectally, intracisternally, intraperitoneally, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The MERS-CoV inhibitor peptides are designed by modification or mutation of a surface structure protein of MERS-CoV in the virus S2 spike region. The heptad repeat regions (HR1 and HR2) of S2 interact to help in fusion of MERS-CoV with cell membranes. The MERS-CoV inhibitor peptide S2 HR2 derivatives were optimized to interfere with the proper mechanism of H R1-H R2 interactions.

The following examples illustrate the present subject matter.

EXAMPLE 1

Synthesis of MERS-CoV Inhibitor Peptides

The sequence of the HR2 region of wild type MERS-CoV is reported in Table 1 as Peptide 1 (SEQ ID NO: 1). This peptide was synthesized and used in assays as a reference or standard against which the activity of new peptides was compared.

To optimize a new sequence related to MERS-CoV HR2 with improved binding potency, computational studies were implemented to generate a set 684 potential candidates by a series of mutations. Free energy-based optimization was computationally carried out to yield a set of top suggested point mutations. Several point mutations were then generated in different combinations with estimated improved binding strength and stability after testing by molecular dynamics experiments. Finally, a set of 11 peptides were synthesized (peptides 2-12 in Table 1).

Several systemic point mutations for every residue in the wild type peptide were generated. Mutations were performed by replacing each amino acid with any other member of the 21 known essential amino acids. All mutations were generated only in MERS-CoV HR2. After each point mutation, the free energy of binding of HR1 and mutated HR2 was calculated as previously described. (Dehouck, Y. et al., "BeAtMuSiC: Prediction of changes in protein-protein binding affinity on mutations," Nucleic Acids Research, 41: pp. W333-W339 (2013)). Candidates with the highest values of binding free energy were synthesized for Anti-MERS-CoV testing (FIG. 1 and Table 1). To confirm binding stability of each peptide after mutation, every HR1-HR2 complex was subjected to a molecular dynamics simulation as previously described. (Kandeel, M. et al., "Molecular dynamics of Middle East Respiratory Syndrome Coronavirus (MERS-CoV) fusion heptad repeat trimers," Computational Biology and Chemistry 75: pp. 205-212 (2018)).

A set of 12 peptides were obtained by custom synthesis service order to Biomatik Inc (Cambridge, ON, Canada) (Table 1). The peptides were HPLC purified and confirmed by mass spectrum to ensure maximum purity and removal of chemicals and byproducts during the peptide synthesis process.

TABLE 1

The sequence of wild type and designed peptides (mutations in bold)

| Name | Peptide Sequence | SEQ ID NO. |
|---|---|---|
| Peptide 1 (WT) | SLTQINTTLLDLTYEMLSLQQVVKALNESYIDLKEL | SEQ ID NO: 1 |
| Peptide 2 | SLTQINTTLLDLTYEMLSLQQVVKALNESYIDLKHL | SEQ ID NO: 2 |
| Peptide 3 | SLTQINTTLLDLTYEMKSLQQVVKALNESYIDLKEL | SEQ ID NO: 3 |
| Peptide 4 | SLTQINWTLLDLTYEMESLQQVVKALNESYIDLKEL | SEQ ID NO: 4 |
| Peptide 5 | SLTQINWTLLDLTYEMESLQQVVKALNEYYIDLKEL | SEQ ID NO: 5 |
| Peptide 6 | SLTQINWTLLDLTYEMESLQQVVKALNEYYIDLKHL | SEQ ID NO: 6 |
| Peptide 7 | SLTQINWTLLDLTYEMESLQQVMKALNEYYIDLKHL | SEQ ID NO: 7 |
| Peptide 8 | SLTQINTTLLDLEYEMLSLQQVVKALNESYIDLKEL | SEQ ID NO: 8 |
| Peptide 9 | SLTQINTTLLDLEYEMRSLQQVVKALNESYIDLKEL | SEQ ID NO: 9 |
| Peptide 10 | SLTQINTTLLDLEYEMRSLEEVVKALNESYIDLKEL | SEQ ID NO: 10 |
| Peptide 11 | SLTQINTTLLDLEYEMRSLEEVVKKLNESYIDLKEL | SEQ ID NO: 11 |
| Peptide 12 | SLTQINTTLLDLEYEMRSLEEVVKKLNESYIDEKEL | SEQ ID NO: 12 |

EXAMPLE 2

Cell-Cell Fusion Assay of MERS-CoV Inhibitor Peptides

Cell-cell fusion assays were performed to quantitate the cell-cell fusion as described previously. (Yamamoto, M. et al., "Identification of Nafamostat as a Potent Inhibitor of Middle East Respiratory Syndrome Coronavirus S Protein-Mediated Membrane Fusion Using the Split-Protein-Based Cell-Cell Fusion Assay," Antimicrob. Agents Chemother. 60(11): pp. 6532-6539 (2016)). Briefly, a pair of 293FT-based reporter cells, effector and target cells, that express individual split reporters (DSP1-7 and DSP8-11 proteins) were used, because DSP1-7 and DSP8-11 produce fluorescence and luminescence only when the two proteins form a tight complex. Effector cells stably expressing DSP8-11 and S-protein and target cells stably expressing DSP1-7 together with CD26 and TMPRSS2 were prepared. Two hours before the fusion assay, both effector and target cells were treated with 6 sM EnduRen (Promega, Madison, Wis., USA), a substrate for Renilla luciferase, to activate EnduRen. Each peptide was dissolved in 10% dimethyl sulfoxide (DMSO) and added to 384-well plates (Greiner Bioscience, Frickenhausen, Germany) using a 12-stage workstation (Biotech, Tokyo, Japan). Next, a Multidrop dispenser (Thermo Scientific, Waltham, Mass., USA) was used to add 50 µl of each single cell suspension ($1.5 \times 10^4$ effector and target cells) to the wells. Incubation was performed at 37° C. for h, then RL activity measurements were obtained with a microplate reader (PHERAStar Plus, BMG Labtech, Cary, N.C., USA).

Figure 2A:
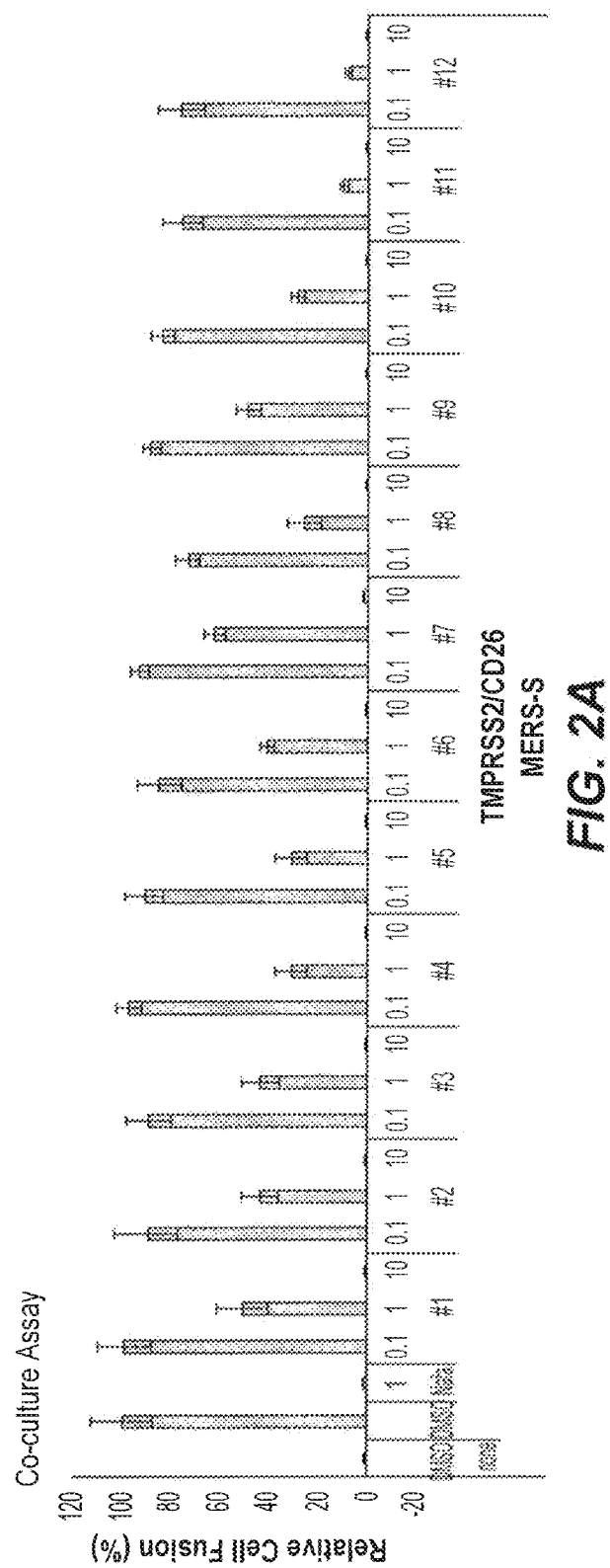
FIG. 2A depicts a graph of the results of a Cell-Cell Fusion Assay measuring the inhibitory properties of Peptides 1-12 at 0.1, 1, and 10 µM.
Figure 2B:
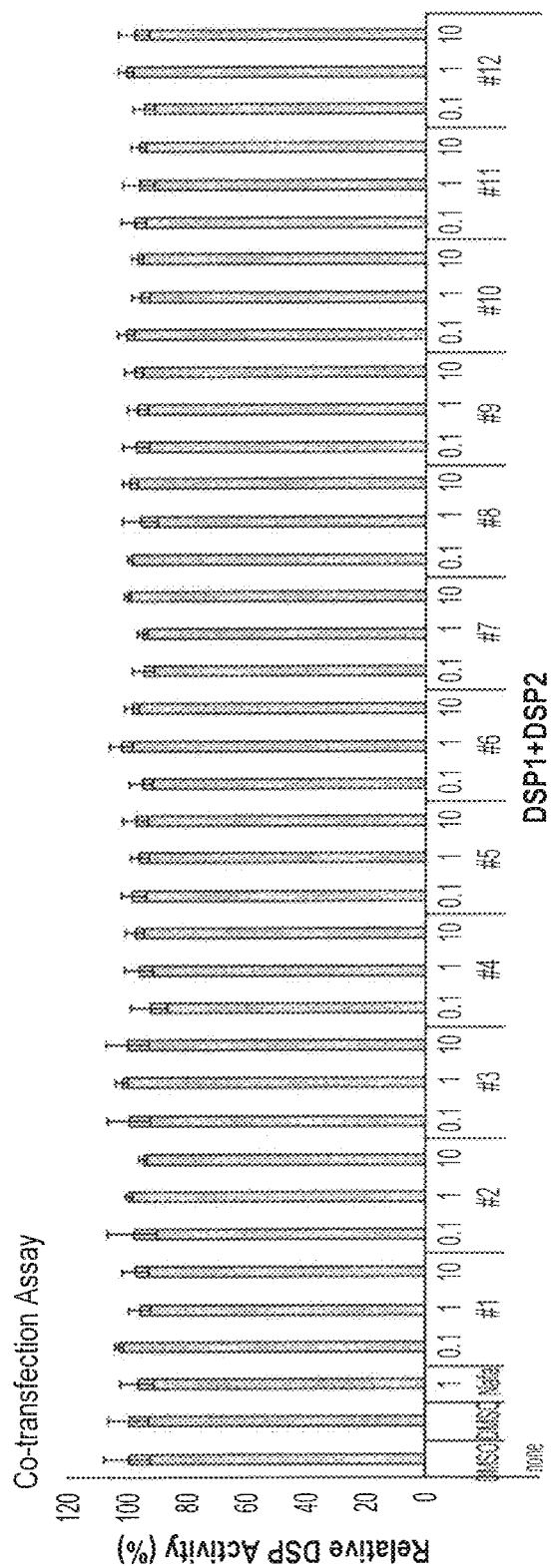
FIG. 2B depicts a graph of the results of a Co-Transfection assay indicating that the Peptides have no interaction with the Cell-Cell Fusion Assay system.

The results indicated strong inhibition of cell-cell fusion at 10 and 1 µM (FIG. 2A). The most potent peptides were peptides 5, 8, 10 and 11, with EC50 values in low and middle nanomolar range (Table 2). Peptides 5, 8, 10 and 11 showed stronger inhibition compared with peptide 1 (the original wild type MERS-CoV sequence). A co-transfection control assay demonstrated that the peptides did not interact with the assay system (See FIG. 2B).

TABLE 2

EC50 values of peptides by using cell-cell fusion assay

| Peptide | EC50 (µM) |
|---|---|
| 1 (SEQ. ID NO:1) | 1.055 |
| 2 (SEQ. ID NO:2) | 0.916 |
| 3 (SEQ. ID NO:3) | 0.938 |
| 4 (SEQ. ID NO:4) | 1.492 |
| 5 (SEQ. ID NO:5) | 0.432 |
| 6 (SEQ. ID NO:6) | 0.917 |
| 7 (SEQ. ID NO:7) | 2.355 |
| 8 (SEQ. ID NO:8) | 0.465 |
| (SEQ. ID NO:9) | 1.299 |
| 10 (SEQ. ID NO:10) | 0.426 |
| 11 (SEQ. ID NO:11) | 0.039 |
| 12 (SEQ. ID NO:12) | 0.831 |

EXAMPLE 3

Plaque Assay of MERS-CoV Inhibitor Peptides

African green monkey kidney cells (Vero cells) were purchased from the American Type Culture Collection (ATCC, Manassas, Va., USA). The cell culture was kept in a $CO_2$ incubator at 37° C. in Dulbecco's modified Eagle's medium (DMEM, Thermo Fisher Scientific, Waltham, Mass., USA) containing 10% fetal bovine serum (FBS, Thermo Fisher Scientific), 25 mM HEPES, 100 U/ml penicillin and 100 µg/ml streptomycin. MERS-CoV was obtained from the Korea Centers for Disease Control and Prevention (CoV/KOR/KNIH/002_05_2015, Permission No. 1-001-MER-IS-2015001).

The plaque reduction assay was performed as reported previously. (Park, B. K. et al., "Generation and characterization of a monoclonal antibody against MERS-CoV targeting the spike-protein using a synthetic peptide epitope-CpG-DNA-liposome complex," BMB Rep. 52(6): pp. 397-402 (2019)). Briefly, Vero cells were cultivated on six-well plates for 12 h at $6 \times 10^5$ cells/well. In an initial study, MERS-CoV was mixed with each peptide at a final concentration of 10 sM for 30 min at 37° C. The mixtures of MERS-CoV and each peptide were added to Vero cells in each well and then incubated for 1 h. After incubation, the supernatants were removed and DMEM/F12 medium (Thermo Fisher Scientific) containing 0.6% oxoid agar was transferred to each well. Four days after infection, plaque formation was observed by staining with crystal violet and plaque numbers were counted (See FIGS. 3A-3O). The initial test results revealed strong inhibition of MERS-CoV by peptides 4, 5, and 6. The other peptides produced a more moderate decrease in plaque formation. Notable results include 98.3% inhibition of plaque formation by Peptide 6, 98.2% inhibition by Peptide 4, 95% inhibition by Peptide 5, 74% inhibition by Peptide 2, and 69-70% inhibition by Peptides 11 and 12. (See Table 3)

TABLE 3

Plaque Inhibition Assay of Peptides 1-12

| Sample | # Plaques | Normalize | Percent of DMSO # |
|---|---|---|---|
| Control | 142 | 568 | 92.20779 |
| DMSO | 154 | 616 | 100 |
| Peptide 1 (SEQ ID NO:1) | 55 | 220 | 35.71429 |
| Peptide 2 (SEQ ID NO:2) | 36 | 144 | 23.37662 |
| Peptide 3 (SEQ ID NO:3) | 55 | 220 | 35.71429 |
| Peptide 4 (SEQ ID NO:4) | 11 | 11 | 1.785714 |
| Peptide 5 (SEQ ID NO:5) | 31 | 31 | 5.032468 |
| Peptide 6 (SEQ ID NO:6) | 8 | 8 | 1.298701 |
| Peptide 7 (SEQ ID NO:7) | 55 | 220 | 35.71429 |
| Peptide 8 (SEQ ID NO:8) | 92 | 368 | 59.74026 |
| Peptide 9 (SEQ ID NO:9) | 81 | 324 | 52.5974 |
| Peptide 10 (SEQ ID NO:10) | 59 | 236 | 38.31169 |
| Peptide 11 (SEQ ID NO:11) | 46 | 184 | 29.87013 |
| Peptide 12 (SEQ ID NO:12) | 48 | 192 | 31.16883 |

Figure 4A:
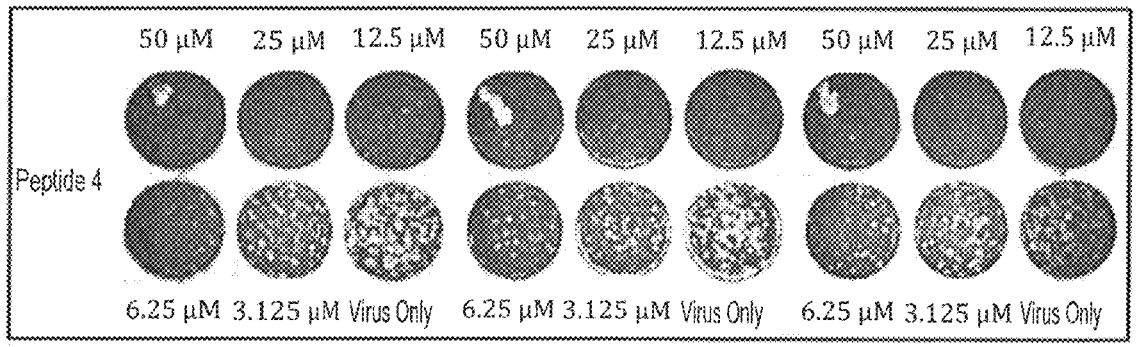
FIG. 4A depicts the results of a Plaque Reduction Assay for MERS-CoV treated with Peptide 4 at 50 µM, 25 µM, 12.5 µM, 6.25 µM, and 3.125 µM.
Figure 4B:
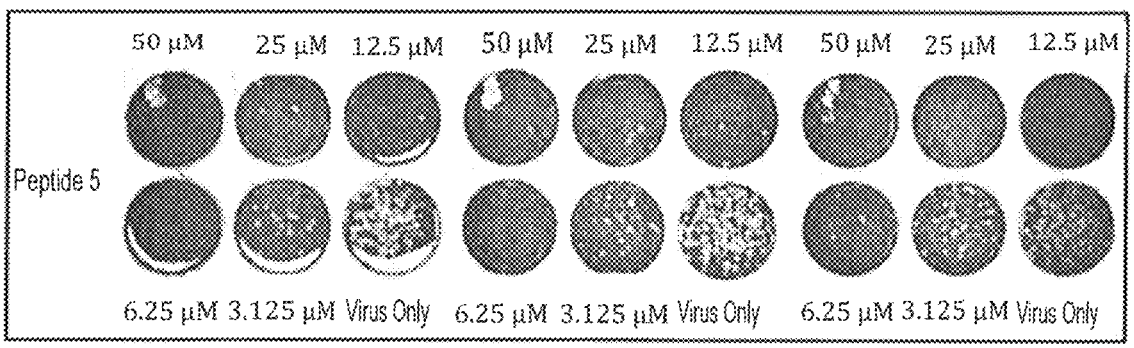
FIG. 4B depicts the results of a Plaque Reduction Assay for MERS-CoV treated with Peptide 5 at 50 µM, 25 µM, 12.5 µM, 6.25 µM, and 3.125 µM.
Figure 4C:
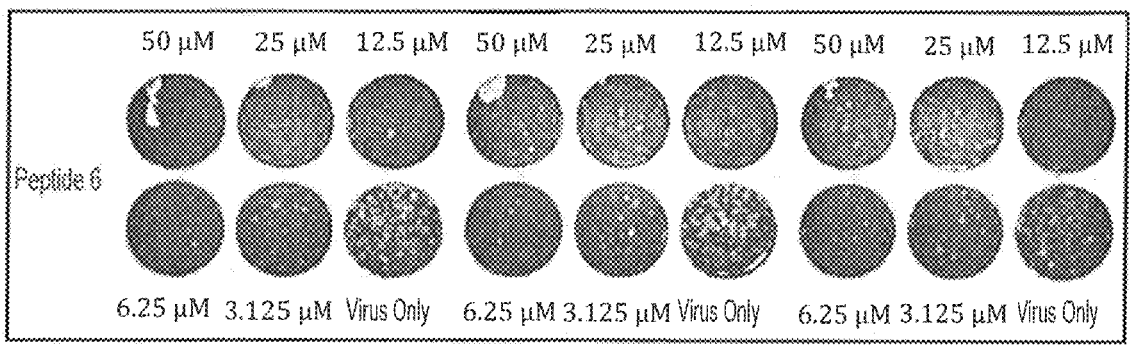
FIG. 4C depicts the results of a Plaque Reduction Assay for MERS-CoV treated with Peptide 6 at 50 µM, 25 µM, 12.5 µM, 6.25 µM, and 3.125 µM.

After initial confirmation of the inhibitory properties of the peptides, Peptides 4, 5, and 6 were tested in varying concentrations, ranging from 50 µM to 3.125 µM (See FIGS. 4A-4C). The results of these experiments were then used to calculate the half maximal effective concentration for Peptides 4, 5, and 6. The results are provided in Table 4.

TABLE 4

EC50 of Peptides 4, 5, and 6.

| Sample | EC50 (μM) |
| --- | --- |
| Peptide 4 | 0.302 |
| Peptide 5 | 1.428 |
| Peptide 6 | 1.849 |

EXAMPLE 4

Cytotoxicity and Viability

Vero cells ($1×10^3$ per well) were plated on 96-well plates and cultured for 12 h. The cells were treated with three fold serial dilutions of Peptides 4, 5, or 6, or with 10% DMSO (control) for 3 days (Peptide concentrations ranged from 100 μM to 0.4 μM). Then, cells were treated with 3-(4,5-dimethylthiazol-2-yl)-2,5-diphenyltetrazolium bromide (MTT, Sigma-Aldrich, St. Louis, Mo., USA) for 4 h at 37° C. Formazan crystals were dissolved in DMSO, and the absorbance at 570 nm was measured using a microplate reader (Thermo Fisher Scientific, Ratastie, Finland).

Figure 5A:
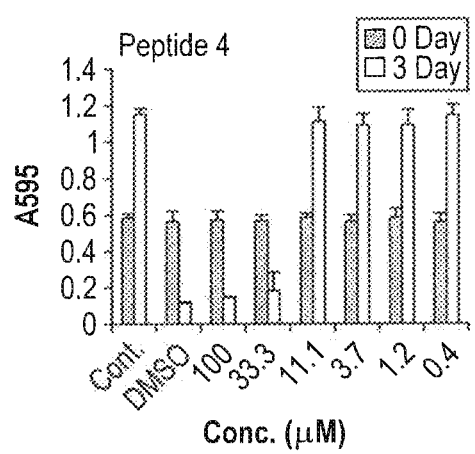
FIG. 5A depicts a graph of the effect of various concentrations of Peptide 4 on the growth of Vero cells.
Figure 5B:
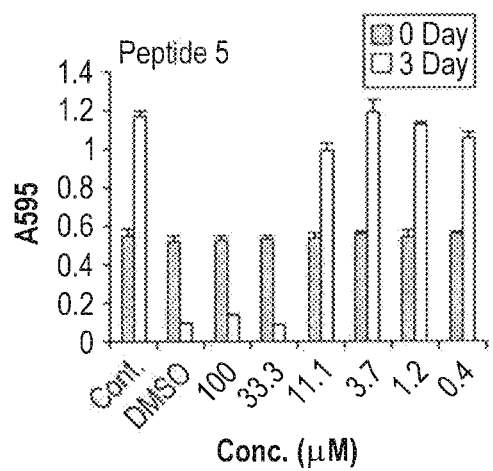
FIG. 5B depicts a graph of the effect of various concentrations of Peptide 5 on the growth of Vero cells.
Figure 5C:
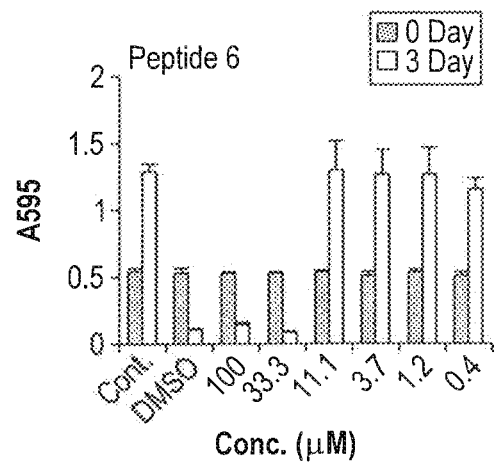
FIG. 5C depicts a graph of the effect of various concentrations of Peptide 6 on the growth of Vero cells.

No cytotoxicity at concentrations equal to or lower than 10 μM was observed for any of the tested peptides (See FIGS. 5A-5C). Thus, it was concluded that Peptides 4, 5 and 6 have a safe cellular profile.

It is to be understood that the MERS-CoV Inhibitor Peptides are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A MERS CoV inhibitor comprising a peptide having the amino acid sequence selected from the group consisting of SEQ ID NOs: 2-8, 10, and 12, and a combination thereof.

2. The MERS CoV inhibitor of claim 1, comprising a peptide having the amino acid sequence of SEQ ID NO: 4.

3. The MERS CoV inhibitor of claim 1, comprising a peptide having the amino acid sequence of SEQ ID NO: 5.

4. The MERS CoV inhibitor of claim 1, comprising a peptide having the amino acid sequence of SEQ ID NO: 6.

5. A pharmaceutical composition comprising the MERS CoV inhibitor of claim 1 and a pharmaceutically acceptable carrier.

* * * * *